(12) United States Patent
Narz

(10) Patent No.: US 8,536,100 B2
(45) Date of Patent: Sep. 17, 2013

(54) RAPID METHOD FOR IDENTIFYING POLYPEPTIDE-NUCLEIC ACID INTERACTIONS

(75) Inventor: Franz Narz, Hilden (DE)

(73) Assignee: Qiagen GmbH, Hilden (DE)

( * ) Notice: Subject to any disclaimer, the term of this patent is extended or adjusted under 35 U.S.C. 154(b) by 129 days.

(21) Appl. No.: 12/922,366

(22) PCT Filed: Mar. 13, 2009

(86) PCT No.: PCT/EP2009/001866
§ 371 (c)(1),
(2), (4) Date: Oct. 25, 2010

(87) PCT Pub. No.: WO2009/112283
PCT Pub. Date: Sep. 17, 2009

(65) Prior Publication Data
US 2011/0065592 A1    Mar. 17, 2011

Related U.S. Application Data

(60) Provisional application No. 61/036,656, filed on Mar. 14, 2008.

(30) Foreign Application Priority Data

Mar. 14, 2008  (EP) .................................. 08004869

(51) Int. Cl.
*C40B 30/00*   (2006.01)
*C12Q 1/68*    (2006.01)
*C12M 1/34*    (2006.01)

(52) U.S. Cl.
USPC ............................. 506/7; 435/6.12; 435/287.2

(58) Field of Classification Search
CPC .................................. C40B 30/00; C12Q 1/68
USPC ............................................................... 506/7
See application file for complete search history.

(56) References Cited

U.S. PATENT DOCUMENTS

2007/0141583 A1 *  6/2007  Li et al. ............................. 435/6

OTHER PUBLICATIONS

Kohzaki and Murakami, ("Faster and easier chromatin immunoprecipitation assay with high sensitivity", Proteomics, 2007, vol. 7, pp. 10-14).*

(Nelson et al., ("Fast Chromatin Immunoprecipitation Assay", Nucleic Acids Research, 2006, vol. 34, No. 1, pp. e2-1 to e2-7)).*
Quantace (Application note (Jan. 5, 2007)).*
Flanagin et al. ("Microplate-based chromatin immunoprecipitation method, Matrix ChIP: a platform to study signaling of complex genomic events", Nucleic Acids Research, 2008, vol. 36, No. 3, pp. e17-1 to e17-9).*
Nelson et al., (Fast Chromatin Immunoprecipitation Assay, Nucleic Acids Research, 2006, vol. 34, No. 1, pp. e2-1 to e2-7).*
International Search Report for PCT/EP200/001866 dated Jun. 8, 2009.
Benotmane et al., "Nonisotopic quantitative analysis of protein-DNA interactions at equilbrum," Analytical Biochemistry, vol. 250:181-185, 1997, XP002931447, ISSN: 0003-2697 (Abstract).
Collas et al., "Chop it, ChIP it, check it: The current status of chromatin immunoprecipitation," Frontiers in Bioscience: A Journal and Virtual Library, vol. 13:929-943, 2006, XP002491454, ISN: 1093-4715.
Craig et al., "A protein-protein binding assay using coated microtitre plates: increased throughput, reproducibility and speed compared to bead-based essays," Journal of Biochemical and Biophysical Methods, vol. 60(1):49-60, 2004, XP002491452, ISSN: 0165-022X.
Desai et al., "Coated microwell plate-based affinity purification of antigens," Analytical Biochemistry, vol. 328(2):162-165, 2004, XP004504044, ISSN: 0003-2697.
Furuya et al., "An immuno-polymerase chain reaction assay for human interleukin-18," Journal of Immunological Methods, vol. 238(1-2):173-180, 2000, XP004195473, ISSN: 0022-1759.
Kohzaki et al., "Faster and easier chromatin immunoprecipitation assay with high sensitivity," Proteomics, vol. 7(1):10-14, 2007, XP002491451, ISSN: 1615-9853 (Abstract).
Oh Sang Wook et al., "Calixarene derivative as a tool for highly sensitive detection and oriented immobilization of proteins in a microarray format through noncovalent moiecular interaction." The FASEB Journal, vol. 19(10):1335-1337, 2005, XP002491453, ISSN: 1530-6860.

* cited by examiner

*Primary Examiner* — Ardin Marschel
*Assistant Examiner* — Richard L Manteuffel
(74) *Attorney, Agent, or Firm* — Fanelli Haag & Kilger PLLC

(57) ABSTRACT

The invention relates to a method for analysing interactions of a nucleic acid with at least one polypeptide, comprising (a) providing a reaction vessel with a composition comprising cross-linked complexes comprising at least one nucleic acid and at least one polypeptide; (b) immobilizing at least part of the cross-linked complexes to the reaction vessel; (c) at least partially reversing said cross-links in said immobilized complexes by performing a heat incubation step thereby at least partially releasing the nucleic acids from the complexes; (d) analyzing the released nucleic acid. wherein steps (a) to (d) are performed in one reaction vessel. Also provided are specific reaction vessels and kits.

14 Claims, 3 Drawing Sheets

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:

-continued

```
<223> OTHER INFORMATION: Primer sequence hsGAPDH_Ex9for319

<400> SEQUENCE: 1
gtctcctctg acttcaaca                                              19

<210> SEQ ID NO 2
<211> LENGTH: 20
<212> TYPE: DNA
<213> ORGANISM: Artificial Sequence
<220> FEATURE:
<223> OTHER INFORMATION: Primer sequence hsGAPDH_Ex9rev394

<400> SEQUENCE: 2
caggaaatga gcttgacaaa                                             20
```

RAPID METHOD FOR IDENTIFYING POLYPEPTIDE-NUCLEIC ACID INTERACTIONS

The invention is related to a method for rapidly identifying interactions of a nucleic acid with at least one polypeptide and is specifically suitable for identifying regions of a genome to which specific polypeptides of interest bind.

Polypeptide-nucleic acid interactions, such as for example protein-DNA interactions are widely involved in a variety of molecular processes of living cells, such as signal transaction, gene transcription, chromosome segregation, DNA replication, recombination and epigenetic silencing of genes. Identifying the genetic targets of DNA binding polypeptides such as transcription factors and knowing the mechanism of polypeptide-DNA interaction are important for understanding cellular processes. Also polypeptide-RNA interactions are an important field of research.

Several methods exist, in order to investigate polypeptide-nucleic acid interactions.

For example Chromatin Immunoprecipitation (ChIP) is a powerful and widely applied technique for detecting the association of individual polypeptides such as proteins with specific genomic regions in vivo. In this technique, living cells are treated with formaldehyde to generate protein-protein and protein-DNA cross-links between molecules in close proximity on the chromatin template in vivo. A whole-cell extract is prepared, and the cross-linked chromatin is sheared by suitable means, such as sonification, mechanical means or enzymatic reactions to reduce the average DNA fragment size to approximately 500 bp. The resulting material is immunoprecipated with an antibody against the protein of interest (for example histones, transcription factors, polymerases), modified (for example acetylated, phosphorylated or methylated) peptide or epitope (in situations, where the protein of interest is epitope-tagged). Immunoprecipitation is usually done using beads, which is a cumbersome and error-prone method. DNA sequences that directly or indirectly cross-link with a given polypeptide (or modified variant thereof) are selectively enriched in the immunoprecipitated sample, due to the cross-linkage. Thus, the method is not restricted to sequence-specific DNA-binding proteins, but any polypeptide-nucleic acid interaction can be detected. Reversal of the formaldehyde cross-linking by heating permits the recovery of the immunoprecipitated DNA. The released DNA is then purified and analyzed by for example PCR and gel electrophoresis in order to identify the regions that were bound by the polypeptides respectively proteins of interest.

Figure 1:
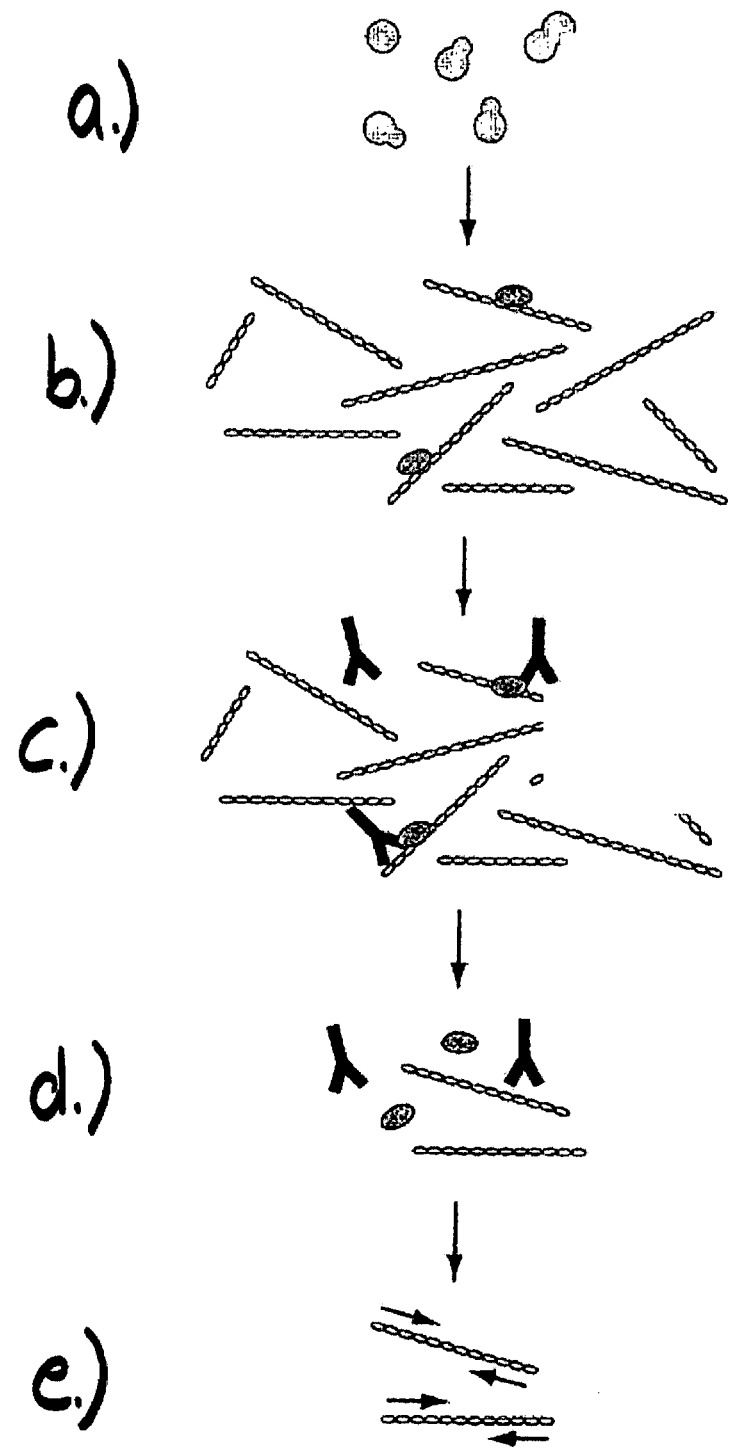

An overview over the standard method used in the prior art is given in FIG. 1. The complete standard ChIP protocol usually takes 2 to 3 days and is therefore time-consuming.

Furthermore, it is desirous, that a respective method not only allows the detection of DNA/polypeptide interactions, but which allows the detection of polypeptide/nucleic acid interactions in general.

Therefore, it is the object of the present invention to provide a more rapid and efficient method for identifying interactions of a nucleic acid with at least one polypeptide.

The problem is solved by a method for analysing interactions of a nucleic acid with at least one polypeptide, which comprises the following steps:
(a) providing a reaction vessel with a composition comprising cross-linked complexes comprising at least one nucleic acid and at least one polypeptide;
(b) immobilizing at least part of the cross-linked complexes to the reaction vessel;
(c) at least partially reversing said cross-links in said immobilized complexes by performing a heat incubation step thereby at least partially releasing the nucleic acids from the complexes;
(d) analyzing the released nucleic acid.

Surprisingly, it was found that it is possible to avoid time-consuming steps for reversing the cross-links in the polypeptide/nucleic acid complexes if a heat incubation step is performed. It was surprisingly found that a respective heating step at least partially releases the nucleic acid from the complex; said released nucleic acid can then be analyzed in step (d). It is e.g. not necessary to purify the released nucleic acid prior to the analysis. Thus, time-consuming steps for reversing the cross-links as are presently performed in the prior art using specific buffers and which take several hours, as well as purification steps can be avoided. This is advantageous, as it is possible to perform the whole method within one day. This is a great improvement over the time-consuming methods that are known in the state of the art.

Furthermore, as it is surprisingly not necessary to purify the nucleic acid after release, it is also possible to perform the whole process (including e.g. amplification reactions) in one reaction vessel. This important advantage is also achieved due to the performed immobilization step (b), wherein at least part of the cross-linked complexes are immobilized to the reaction vessel. This feature allows processing of the sample in a single reaction vessel if desired. This saves material, hands-on time and is convenient for the user.

Accordingly, it is preferred that the nucleic acid that is released in the cross-link reversing step (c) is not isolated or purified prior to step (d). Of course, one may perform washing steps while the cross-linked complexes are still bound/immobilized to the reaction vessel in order to remove the remaining/unbound components. However, it is preferred that no affinity or precipitation purification/isolation of the released nucleic acid is performed. Preferably, steps (a) to (d) are performed in one reaction vessel, thereby avoiding transfer steps to other vessels. Thus, using the same reaction vessel for all steps has significant advantages.

The released nucleic acid can be analyzed by many different methods and means. E.g. amplification reactions (e.g. isothermal amplification or PCR) can be performed in order to identify the released nucleic acid and thus the region where the polypeptide interacted with the nucleic acid. Depending on the experimental set-up, the amplified products can e.g. be cloned into a vector and can be identified by a sequencing reaction. Also, specific primers could be used in order to amplify the released nucleic acid in the sample (if present), wherein an amplification reaction product indicates that the specific nucleic acid was released from the cross-linked complexes. The released nucleic acid can also be analyzed by hybridization techniques, e.g. on microarrays carrying different probes, e.g. polynucleotides. E.g., the released nucleic acid could be labeled and used in a microarray set up. Hybridization of the labeled released nucleic acid to a specific polynucleotide of the microarray allows the identification of the nucleic acid region where the polypeptide of interest interacted with the nucleic acid. Also, many other experimental set-ups and analyses are conceivable and available for the skilled person.

According to a preferred embodiment, the released nucleic acid is identified in step (d) by an amplification reaction. Preferably by a PCR (polymerase chain reaction) step. Performing a PCR reaction in order to identify the released nucleic acid is very advantageous as it allows very rapid processing in a single reaction vessel. E.g. one may perform the cross-link reverse step (c) and the amplification step (d) as elements of a HotStart polymerase chain reaction protocol. Hot-start PCR is a technique that reduces non-specific amplification during the initial set up stages of the PCR. The technique may be performed manually by heating the reaction components to the melting temperature (e.g. 94° C.) before adding the polymerase. Specialized enzyme systems have also been developed that inhibit the polymerase's activity at ambient temperature, either by the binding of an antibody or by the presence of covalently bound inhibitors that only dissociate after a high-temperature activation step. Any hot start variant can be used according to the principles of the present invention. It was surprisingly found, that an initial heat incubation step e.g. at $\geq 80°$ C. and preferably $\geq 90°$ C. as is used in a HotStart PCR reaction is sufficient in order to release nucleic acid(s) from the cross-linked complex(es). This is very convenient for the user, because after performing the incubation step (b) in order to immobilize the cross-linked complexes of interest to the reaction vessel, the necessary PCR components (e.g. primers, nucleotides, enzymes) can be directly added to the reaction vessel comprising the immobilized, cross-linked complexes in order to perform the PCR reaction. No additional steps/measures are necessary in order to reverse the cross-links and to release the nucleic acid. A regular HotStart PCR protocol surprisingly results in a release of nucleic acids from the cross-linked complexes. The released nucleic acids can be directly used as a template for the PCR reaction. A HotStart PCR protocol regularly comprises a heating step, wherein the reaction mix is incubated at approximately $\geq 90°$ C. for usually 10 to 20 minutes in order to e.g. activate a heat sensible taq polymerase. It was surprisingly found that this activation step is sufficient in order to at least partially release the nucleic acid from the cross-linked complex and to perform the PCR reaction using the unpurified released nucleic acid as a template. This rapid protocol is a great advantage over the methods known in the prior art.

The heat incubation in step (c) is preferably performed for at least 5 minutes, at least 10 minutes, at least 15 minutes or at least 20 minutes. Preferably, the incubation step (c) is performed between approximately 10 to 30 minutes, approximately 10 to 20 minutes and approximately between 10 to 15 minutes. The temperature used in the heat incubation step is preferably above $\geq 80°$ C., $\geq 85°$ C., $\geq 90°$ C. and more preferably $\geq 94°$ C.

The polypeptide/nucleic acid complex needs to be precipitated. In the prior art, this is usually done by adding capture antibodies specific for the polypeptide of interest. In order to precipitate the capture antibody, for example magnetic beads comprising binding agents having a specificity against the capture antibody are used in the prior art. However, the use of magnetic beads is time-consuming and error-prone, as several washing steps are necessary and beads comprising bound complexes can be lost. Furthermore, as outlined above, it is advantageous if all reaction steps can be performed in a single reaction vessel. Therefore, in step (b) of the method according to the present invention, the cross-linked complexes are immobilized to the reaction vessel. This is advantageous over methods using magnetic beads or similar devices, as the risk to loose immobilized cross-linked complexes is reduced as they are basically contained in the reaction vessel. There are several alternatives provided with the present invention, in order to immobilize the cross-linked complexes to the reaction vessel.

According to a preferred embodiment, the reaction vessel carries at least one capture agent specific for a component of the cross-linked complex, preferably for the polypeptide of interest. Said capture agent can be immobilized and thus affixed to the reaction vessel using e.g. standard methods known in the prior art. A respective reaction vessel carrying capture agents can be for example obtained by coating the reaction vessel with the capture agent. Thereby a reaction vessel, having a specific capture surface is provided. When the cross-linked complexes comprising at least one nucleic acid and at least one polypeptide are contacted with the reaction vessel and are incubated, the capture agents immobilized to the reaction-vessel bind to the respective component of the cross-linked complex, usually the polypeptide, thereby immobilizing the target cross-linked complexes specifically to the reaction vessel. Complexes which do not comprise the polypeptide of interest are not bound and thus not captured/immobilized to the reaction vessel. Washing steps can then be performed in order to separate unbound material. As the cross-linked complexes are immobilized to the reaction vessel due to the capture agents, the risk of undesirable loss of complexes is prevented/reduced. This method has the advantage that it is very easy to perform and that all steps can be performed within one reaction vessel.

According to a further embodiment, the cross-linked complexes comprising at least one nucleic acid and at least one polypeptide are contacted with a capture agent specific for a component of the cross-linked complex, preferably the polypeptide component. However, the capture agent is not immobilized to the reaction vessel according to this alternative. Instead, a reaction vessel is used, which carries an immobilized linking agent which binds the used capture agent. Upon binding of the linking agent to the capture agent, the target cross-linked complexes comprising at least one nucleic acid and at least one polypeptide are immobilized to the reaction vessel via the capture agent which is bound/captured by the linking agent and thus immobilized to the reaction vessel. When using this embodiment it is advantageous to choose a linking agent, which recognizes a conserved part of the capture agent (for example the constant region of an antibody) as this allows the use of the same linking agent for different capture agents. A respective embodiment is e.g. useful for multiplex applications, as will be described in further detail below.

It is also within the scope of the present invention to use a combination of capture and linking agents within one reaction vessel. A respective embodiment could be e.g. advantageous for experimental settings, wherein the interaction of different polypeptides with nucleic acids is analyzed within one reaction vessel.

The reaction vessel may carry at least two different binding and/or capture agents. According to one alternative, said binding or capture agents have a specificity for different polypeptides or for different parts of the polypeptide(s) of interest. According to one alternative, the used capture agents bind different polypeptides. This embodiment allows for example the detection of more than one polypeptide/nucleic acid interaction in one experiment. E.g. the interaction of two or more different polypeptides with nucleic acids can be analyzed. According to a different embodiment, said capture agents bind different variants of the same polypeptide (for example histones) or bind at different regions of the same polypeptide.

Thereby it is ensured that the binding reaction and accordingly the immobilization of the cross-linked complexes to the reaction vessel is as efficient/quantitative as possible. This ensures that the maximum amount of target complexes can be bound even if some epitopes are not accessible for some capture agents, e.g. as they are masked due to the cross-linking. E.g., one could use polyclonal antibodies in order to provide different capture agents that bind the same target polypeptide.

A further example wherein the use of different capture agents in one reaction vessel can be useful is the analysis of protein families. E.g. if an analysis is desired whether specific regions of a gene are recognized/bound by specific polypeptides (e.g. polymerases), one could use a mixture of capture agents which recognise the different polypeptides of interest (e.g. RNA Pol II and RNA Pol III). In a respective setting one would capture any nucleic acids that are recognized/bound by these polypeptides. Of course, one could also perform a respective analysis using one capture agent in one reaction vessel (and basically adding/comparing the individual results).

The method according to the present invention is especially suitable for a multiplex format, as multiplexing can easily and conveniently be performed. It is for example possible to coat different reaction vessels of a multiplex format with different capture and/or linking agents such as antibodies and to perform e.g. multiplex PCR reactions in the reaction vessels. As is outlined above, it is also possible and within the scope of the present invention to use more than one capture agent within one reaction vessel. As was outlined above, it is also possible to use a format wherein each reaction vessel is at least partially coated with the same linking agent, which is specific for a conserved region of different capture agents, which are specific for different polypeptides of interest. As the conserved region of the capture agent is bound/recognized according to this embodiment, it is possible to use the same binding agent for different capture agents. A respective multiplexing format is e.g. advantageous for a kit format, where the end user wants to use or combine his "own" specific capture agents/antibodies for a particular polypeptide of interest. With this embodiment, the user can use the pre-coated reaction vessels—which are convenient to use—but remains flexible regarding the use of different capture agents, e.g. antibodies being specific for the polypeptide of interest but carrying a conserved region which is recognized by a universal linking agent. However, it is also within the scope of the present invention that the user performs the coating step in order to prepare the reaction vessel(s).

As was outlined above, the reaction vessels can be coated with the capture agents or respectively the linking agents via immobilization of the capture agents or the linking agents to the reaction vessel. Several methods can be used in order to apply the capture/binding agents to the reaction vessel.

One option is an unspecific adsorption. Capture/binding agents, which are usually polypeptides, bind unspecifically to a variety of polymers (e.g. polystyrene polypropylene, polycarbonate) common reaction vessels are usually made of, if the hydrophobicity is reduced. For the present embodiment, wherein a PCR reaction is performed, it is preferred that reaction vessels are used that have good polypeptide binding properties as well as optical characteristics, in order to be compatible with common PCR machines (e.g. TopYield Module of NUNC). According to one embodiment the capture agents such as antibodies are slightly diluted in a buffer, preferably a carbonate buffer having a pH above 7 and are added to the reaction vessel. Also other buffer systems, e.g. ELISA buffers can be used according to the present invention in order to coat the vessel.

Also within the scope of the present invention is the use of linkers, including the above described linking agents (e.g. protein A or G, anti-immunoglobulin antibodies, streptavidine for biotinylated antibodies/capture agents). To use a respective linker is advantageous as the binding region of the capture agent is directed towards the opening of the reaction vessel and is e.g. not directed towards the wall of the reaction vessel. The capture agents can be arranged in an ordered fashion. Preferably most of the capture agents or even all of the capture agents are respectively oriented. This leads to an increased binding capacity as the capture agents are immobilised in a rather oriented fashion.

Preferably, after coating of the reaction vessels with the capture/linking agents or linkers, the remaining free sides of the reaction vessel are blocked. A respective blocking step is advantageous, as cross-linked complexes (not comprising the target) may bind unspecifically to unblocked sites of the reaction vessel thereby increasing unspecific background reactions which should be avoided. Blocking agents that could be used are e.g. albumins (e.g. BSA), serum (e.g. newborn calf serum), casein or certain milks, detergents, in particular non-ionic detergents such as Tween 20, proteins, nucleic acids which do not interfere with the ones to be analyzed (e.g. tRNAs) or other suitable macromolecules. The blocking reagents are solved in a suitable buffer (e.g. an alkaline carbonate buffer) so that they are present in excess and are added to the reaction vessel. After incubation, the remaining blocking solution is removed and the reaction vessel is preferably washed. The reaction vessel is then ready to use.

The analysis in step (d) is usually performed in order to identify the released nucleic acid and thus the regions on the nucleic acid, where the polypeptide of interest binds respectively was bound. According to one embodiment, step (d) comprises a PCR amplification reaction using the released nucleic acid as template and using oligonucleotide primers which specifically amplify a certain region of the nucleic acid of interest, wherein a PCR product is generated if the released nucleic acid comprises said certain region. For example, in case chromatin is analyzed the certain region of the nucleic acid corresponds to a certain region of the genome that is of particular interest.

In order to identify unknown nucleic acids, several strategies can be used. E.g. a PCR amplification can be performed using adapters which also comprise a universal priming site, thus allowing the amplification of the unknown nucleic acid sequence using primers recognising the universal priming site in the adapter. The PCR products can also be cloned into suitable vectors, e.g. via TA cloning, TOPO cloning or similar methods. The cloned PCR products (and accordingly the nucleic acid regions where an interaction with the polypeptide occurred) are then sequenced and accordingly identified. Alternatively, the released nucleic acids which correspond to the regions where an interaction with the polypeptide occurs, is identified by hybridisation techniques. Optionally, the released nucleic acids are amplified and labelled prior to hybridisation (e.g. using microarrays or southern blot techniques).

The composition comprising cross-linked complexes comprising at least a nucleic acid and at least a polypeptide may be obtained by
 i) incubating cells containing at least one complex comprising nucleic acids and polypeptides with a reversible cross-linking agent at an appropriate concentration to cross-link said complex;
 ii) optionally stopping the cross-linking reaction;
 iii) lysing said cells and shearing said nucleic acid.

Basically all agents can be used as cross-linking agents which are able to diffuse into cells and/or tissue and which make covalent cross-links between functional groups of nucleic acids and polypeptides. Suitable cross-linking agents are for example formaldehyde or glutaraldehyde. Cross-linking can thus be performed by incubating cells with formaldehyde at room temperature or at elevated temperatures such as 37° C. with gentle rocking for several minutes, usually between 5 to 20 minutes. Tissue fragments may need longer incubation. Once the cross-linking reaction is completed, the cross-linking agent can be removed. E.g. the cross-linking reaction can be stopped, for example by adding an inhibitor of cross-linking agents such as e.g. glycine. If used, said inhibitor is usually added at a molar concentration equal to the cross-linking agent or in excess. In case the cross-linking agent is formaldehyde in a concentration from about 0.5% to 10%, glycine in a concentration of 0.1 M to 1M may be used. However, also other cross-linking agents, inhibitors in different concentrations can be used.

Cells can then be collected and lysed. Lysis can be achieved mechanically (e.g. by shearing or ultrasound). Lysis can also be induced by chemical agents. Suitable lysis buffers are well known in the prior art and may comprise e.g. detergents such as Tx-100 and Tween, salts containing for example a sodium salt, EDTA and detergents such as SDS. However, when choosing a lysis buffer, it should be ensured that the polypeptides in the sample are not denatured as this could prevent recognition and thus binding of the capture agent to the polypeptide component of the complexes. Chemical lysis and mechanical lysis methods can also be combined. The lysis buffer should be chosen such that the cells are opened and the nucleus is released but that the proteins are not denatured. Several suitable lysis methods are known to the skilled person.

Tissue fragments can be homogenised before lysing. In order to obtain fragmented cross-linked complexes of nucleic acids and polypeptides, a shearing step is preferably performed. Thereby an appropriate length of the nucleic acid fragment is obtained. Shearing can be done for example mechanically, chemically or enzymatically. Mechanical shearing of the nucleic acids can be performed by nebulization or sonication; sonication is preferred. Enzymatical shearing of DNA can be performed e.g. by using DNAse I in the presence of Mn salt or by using micrococcal nuclease in presence of Mg salt to generate random DNA fragments. The conditions of cross-linked DNA shearing can be optimized based on cells and sonicator equipment or digestion enzyme concentrations. Respective methods are well-known in the prior art and thus need no further description.

Once DNA shearing is completed, cell debris can be removed e.g. by centrifugation, and the supernatant containing the cross-linked nucleic acid/polypeptide complex is collected and used for the subsequent immobilization reactions.

The method of the present invention can be used in order to identify interactions of at least one nucleic acid with at least one polypeptide in a living cell (see description above and below) but also in order to analyze respective interactions in vitro. For in vitro applications, e.g. the polypeptide(s) of interest can be added to a nucleic acid or a nucleic acid mixture in order to analyze if and where an interaction occurs. Cross-linking can be performed and the cross-linked complexes are immobilised to the reaction vessel and processed as described herein. There are no limitations. Furthermore, the present invention can be used in order to study polypeptide/DNA interactions as well as polypeptide/RNA interactions. In case the interaction with RNA is analyzed, the amplification reaction usually comprises a reverse transcription step in order to transcribe the RNA released from the cross-linked complex into cDNA which can then be used as template in the amplification reaction. Otherwise, the protocols are basically the same.

Depending on the desired analysis, it should be adapted, which part of the cells is extracted.

In case the analysis aims at analysing nucleic acids which are predominantly present in specific cell compartments, it can be advantageous to perform suitable enrichment steps. E.g. a common procedure to enrich chromatin comprises a mild lysis of the cells, which leaves the nuclei intact (e.g. using detergents or mechanical lysis procedures), isolation of the nuclei by performing at least one centrifugation step and subsequently, lysis and shearing/fragmentation of the nuclei. A further example is the interaction of polypeptides with nucleic acids that are coded in the mitochondria. E.g. one could perform a differential detergent extraction which leaves the mitochondria intact. The mitochondria can then be isolated by centrifugation. A further example is the interaction of the proteins with mRNA (e.g. translation factors). One could perform a mild lysis which leaves the nucleus intact and only permeabilizes the cell membrane (e.g. by hypotonic lysis). The nuclei and the insoluble components are then removed and the capture reaction is performed with the cytoplasma fraction.

Also provided with the present invention is a reaction vessel comprising a capture agent specific for a polypeptide of interest which is immobilized to the reaction vessel, wherein the specific binding regions of the capture agent are preferably orientated towards the opening of the reaction vessel. Preferably, most of the capture agents are respectively oriented. A respective reaction vessel can be used in order to immobilize cross-linked complexes comprising at least one nucleic acid and at least one polypeptide in order to study the interactions. A respective reaction vessel has the advantage that the immobilisation/precipitation steps as well as the amplification steps (e.g. PCR) can be done within said reaction vessel. A respective reaction vessel can thus be used in the method according to the present invention. As outlined above, it is not necessary to purify and separate the released nucleic acids. Methods in order to obtain/manufacture respective vessels (e.g. coating procedures) are described above and below.

Also provided is a kit for analysing interactions of a nucleic acid with at least one polypeptide, which comprises a reaction vessel according to the present invention. A respective kit may also comprise at least one of the following components:
  capture agents;
  buffers;
  cross-linking agents;
  releasing agents;
  washing buffers;
  PCR components;
  reaction vessels.

A "nucleic acid" is a polymer of nucleotides which are usually linked from one deoxyribose or ribose to another and refers to DNA as well as RNA, depending on the context. The term "nucleic acid" does not comprise any size restrictions and also encompasses polynucleotides comprising modifications.

The term "polypeptide" refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity or bioactivity, including e.g. bioactive polypeptides such as enzymatic proteins or peptides (e.g. nucleic acid processing polypeptides such as nucleasen and polymerasen), transcription factors, translation factors, nucleic acid binding polypeptides such as histones. The polypeptides whose interaction can be analyzed with the method according to the present invention somehow interact with nucleic acids—either sequence specific or unspecific—and can thus be cross-linked to complexes of nucleic acid and polypeptide upon addition of a cross-linking agent.

A "reaction vessel" is any area or compass allowing the reception of the cross-linked complexes of nucleic acids and polypeptides. Examples of suitable reaction vessels are sample storage vessels, reaction and collection vessels and plates, multi-well plates, micro titer plate wells, tubes, microtubes, tubes for PCR, PCR strips and wall less vessels such as array samples comprising hydrophilic and hydrophobic zones.

The linking agents and capture agents according to the present invention may be of any nature and may have any structure, as long as they are able to specifically recognize and bind their target which is usually the polypeptide of the complex of nucleic acid and polypeptide of interest. They may be selected from the group consisting of immunoglobulin molecules or fragments thereof, such as antibodies, antibody fragments or variants thereof having a binding function, linking agents having a protein scaffold providing a binding function such as for example anticalines, aptamers, transcription factors, enzymes and the like.

An overview over compounds, which have a similar binding function as antibodies is given in Hey, et al: Artificial, non-antibody binding proteins for pharmaceutical and industrial application, Trends in Biotechnology, Vol 23 No. 10, October 2005 page 514-522, herein incorporated by reference. An antibody fragment is any fragment of an antibody comprising at least 20 amino acids from said whole antibody, preferably at least 100 amino acids which still has a binding capacity. In a preferred embodiment the antibody fragment comprises the binding region of the antibody such as a Fab fragment, a F(ab)2 fragment, multibodies comprising multiple binding domains such as diabodies, triabodies or tetrabodies, single domain antibodies or affibodies. An antibody variant is a derivative of an antibody or antibody fragment having the same binding function but e.g. an altered amino acid sequence.

According to one embodiment, the binding and/or capture agent is an antibody. The use of antibodies has the advantage that they can be easily generated by e.g. administering the polypeptide of interest to an animal to effect a specific immunogenic response to said polypeptide of interest. The animal may be selected from the group consisting of mouse, rat, rabbit, chicken, guinea pig, goat and sheep. The antibody may be a monoclonal or a polyclonal antibody. Suitable methods for obtaining respective antibodies are described in "Antibodies—A laboratory Manual" by Ed Harlow and David Lane, 1988 and/or "Monoclonal antibody protocols" by W. C. Davies, 1995, herein incorporated by reference. Due to the higher specificity of monoclonal antibodies, monoclonal antibodies are usually preferred. Monoclonal antibodies may be obtained by recovering at least one antibody producing cell from an animal which was immunized with the polypeptide of interest, immortalizing said antibody producing cell and isolating a monoclonal antibody from the immortalized antibody producing cell.

The method of the present invention is further illustrated by the following figures and examples:

FIG. 1 shows the ChIP principle as it is usually performed in the prior art. In step a) whole-cells are cross-linked with formaldehyde. In step b) whole-cell extracts are prepared and sonicated in order to shear and solubilize the chromatin.

In step c), immunoprecipitation takes place, with antibodies which specifically bind the proteins (for examples histones) which bind in turn to the genomic DNA.

Immunoprecipitation is usually done in the prior art by using magnetic beads. For example, the beads can be coated with protein A or G. Following immunoprecipitation, the DNA is washed and then the cross-linking is reversed in step d). The proteins are removed by proteinase K treatment. Afterwards, the DNA is purified for example by using affinity columns.

The purified DNA is then analyzed by PCR. The complete protocol takes 2 to 3 days.

Figure 2:
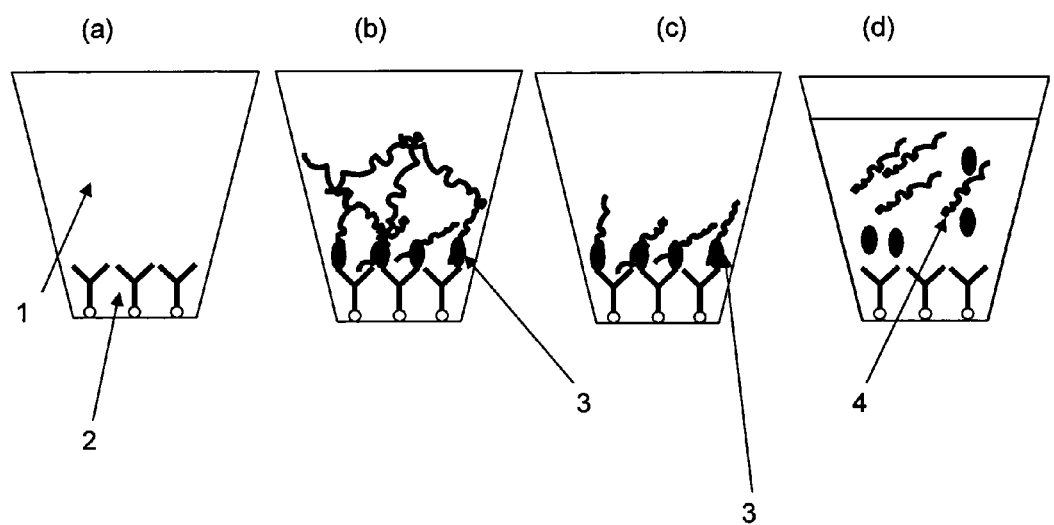

FIG. 2 illustrates the principle according to the present invention according to one embodiment, wherein a capture agent specific for a polypeptide of interest, e.g. histones, is used:

In step (a) the reaction vessel (1) is coated with capture agents (2) specific for the polypeptide of interest, in the shown embodiment an antibody. This reaction vessel (1) is contacted with a composition comprising a mixture of different cross-linked complexes (3) of nucleic acids and polypeptides. Respective complexes (3) can be obtained by using methods commonly known in the state of the art, which are also described above. During incubation, the cross-linked complexes (3) comprising the polypeptides of interest are bound by the capture agents (2) and therefore immobilized/fixed to the reaction vessel (1). Washing steps are performed in order to eliminate unbound material such as e.g. cross-linked complexes which do not comprise the polypeptide of interest and which accordingly are not bound by the capture agents (2) (see steps (b) and (c)).

Next (step d), a PCR mastermix and primers are directly added to the reaction vessel (1) and a HotStart PCR is performed. The HotStart step has the effect that cross-linking is reversed in the complex (3), thereby releasing the nucleic acids (4) and the polypeptides from the cross-linked complexes. The PCR can then directly be performed. In contrast to the methods known in the state of the art, all steps are done in one reaction vessel. No other systems or components are needed, which saves hands on time and costs for the components. No purification of the released nucleic acid is necessary prior to performing the PCR reactions. The released nucleic acid is suitable as template. Therefore, the method of the present invention is particularly suitable for multiplex analysis.

The method of the present invention is also outlined in further detail by the following non-limiting examples:

EXAMPLES

Used Abbreviations

RT: room temperature
PBS: Phosphate buffered saline
PBST Phosphate buffered saline+Tween 20
TBS: Tris buffered saline
TBST Tris buffered saline+Tween 20
TE: Tris HCl buffer with EDTA
LS buffer: low salt buffer
IP: Immunoprecipitation
BSA: bovine serum albumin
HRP: horse radish peroxidise
Rev: reverse
Fwd: forward Example 1

That the method according to the present invention allows the specific analysis of nucleic acid/polypeptide interactions is shown by the following experiment, using an antibody against RNA Pol II. RNA Pol II is associated with all transcriptional active genes and the GAPDH gene is constitutively active in many cells, such as MCF7 cells. Accordingly, GAPDH gDNA should be enriched using the specific antibody against RNA Pol II. For comparison, an unspecific antibody was used.

Step 1: Preparation of Chromatin

A 90% confluent T75-flask of MCF7 cells (~$10^7$ cells) are fixed by removing the cell culture medium and adding 20 ml serum free medium supplemented with 37% formaldehyde. After 15 min incubation at RT fixation is stopped by removing the fixative and adding 10 ml of fixing-stop-solution (1 ml 10× Glycine-stock (Active Motif), 1 ml 10×PBS, 8 ml $H_2O$). Fixed cells are washed with 10 ml PBS and harvested in 5 ml PBS using a cell scraper. Chromatin is prepared as follows:
- 10 min centrifugation at 782 g
- Resuspend pellet in 1 ml IP Puffer (150 mM NaCl, 0.5% NP-40, 1% Triton×100, 5 mM EDTA, 50 mM Tris.HCl (pH 8), 0.5 mM DTT)
- Incubate 30 min on ice
- sonicate to fragment chromatin (20 pulse a 20 sec)

Step 2: Coating of the Reaction Vessel

TopYield modules (Nunc) can be used as multiplex vessels which are suitable PCR strips which can also be easily coated with capture agents.

The following components are added:
- anti RNA Pol II antibody (Santa Cruz sc-899) and goat anti mouse IgG~HRP (Sigma) are diluted 1:200 in Coating Buffer (4.3 g $NaHCO_3$, 5.3 g $Na_2CO_3$ ad 1 l, pH 9.4)
- 50 µl diluted antibody are added per Top Yield well
- Incubate 1 h 37° C.
- Blocking free sides of the reaction vessels using either 240 µl BSA Blocking Buffer (8 g NaCl, 1.42 g $Na_2HPO_4*2H_2O$, 0.2 g $KH_2PO_4$, 0.2 g KCl, 5 g BSA ad 1 l, pH 7.4) or Microplate Blocking Buffer (2% sucrose, 0.1% BSA, 0.9% NaCl (w/v) in PBS)
- Incubate 1 h 37° C.
- 4×1 min wash with Chimera Buffer B (Chimera Biotec)
- add 50 µl chromatin as prepared in example 1
- incubate over night 4° C. or at 37° C. for 1 h (also other incubation times and settings can be used)
- wash 3× with LS buffer (150 mM NaCl, 0.5% Deoxycholat, 0.1% SDS, 1% NP-40, 1 mM EDTA, 50 mM Tris.HCl pH 8)
- wash 3× with Taq-buffer (500 mM Tris/Cl, 200 mM KCl, 50 mM $(NH_4)_2SO_4$ 15 mM $MgCl_2$, ad pH 8.7)

Step 3: PCR Analyis

For performing the PCR reaction, add per well
- 25 µl SYBR Green Master Mix (QIAGEN)
- 0.3 µM GAPDH Primer (Rev/Fwd, final conc.)
- 15 µl H2O Primer sequences for GAPDH:

```
hsGAPDH_Ex9for319
GTCTCCTCTGACTTCAACA      (Seq. ID. No. 1)
```

```
hsGAPDH_Ex9rev394
CAGGAAATGAGCTTGACAAA     (Seq. ID. No. 2)
```

Cycling protocol (Hot Start) in an Opticon II real-time cycler (BioRad):
1: 95° C. 15 min
2: 94° C. 15 sec
3: 55° C. 30 sec
4: 72° C. 30 sec
45 cycles 2→34

Figure 3:
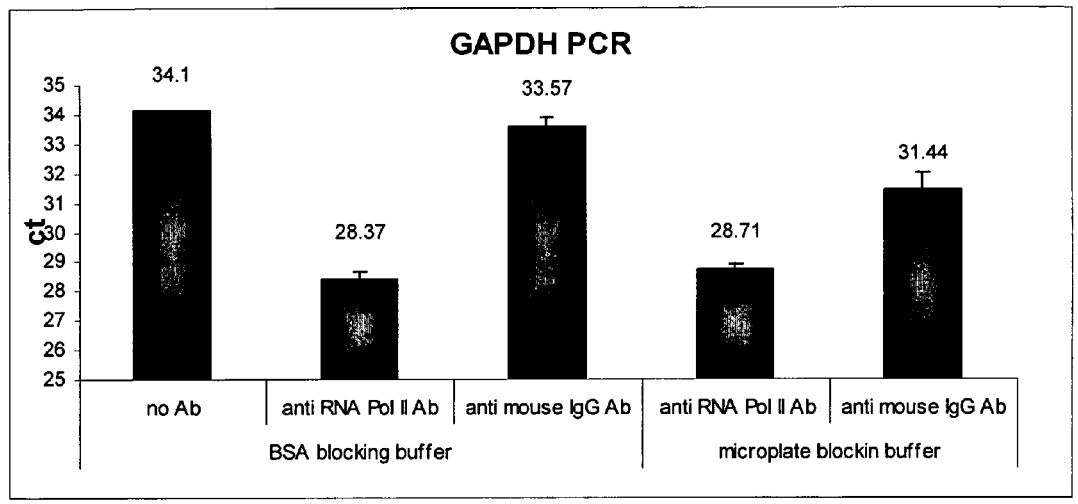

FIG. 3 shows the result. As RNA Pol II is associated with all transcriptional active genes and the GAPDH gene is constitutively active in MCF7 cells, GAPDH gDNA should be enriched using a RNA Pol II antibody. The cT values of the RNA Pol II wells are up to 5 cT's lower compared to the wells were the unspecific anti IgG antibody was used, which indicates that indeed more RNA Poll II bound GAPDH gDNA was bound in these wells. This shows that is not necessary to reverse the cross-linking and to purify the DNA. Just by addition of PCR mastermix and the initial PCR activation step of 15 min at 94° C. is sufficient to release the bound DNA.

Example 2

Another example analyzing the effect of different washing buffers also shows the proof of concept:

The experiment was performed as described above. After chromatin binding different washing buffers were used:

For the first three washing steps either LS buffer or TBST (10 mM Tris-HCl, 150 mM NaCl, pH 7.5, 0.1% Tween 20) were used.

For the second three washing steps either Taq-buffer or TE (10 mM Tris-HCl pH 8; 1 mM EDTA) were used.

Figure 4:
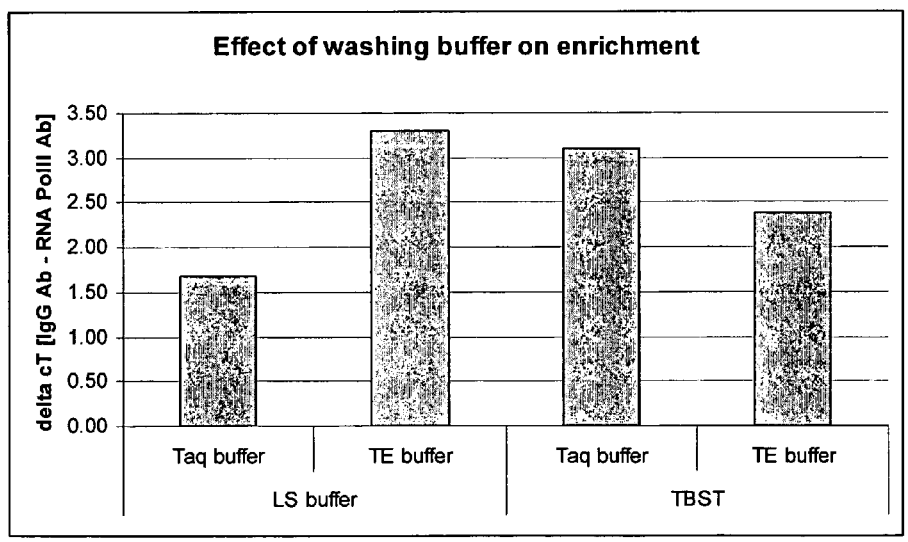

FIG. 4 shows the results. Shown is the delta between the cT's obtained using the specific RNA Pol II antibody and the unspecific anti-mouse IgG antibody. With all three washing procedures, an enrichment could be observed (delta cT>0). The largest enrichment was achieved using the combination of LS buffer with TE (delta cT of 3.3). A delta cT of 3 indicates, that 8 times more GAPDH gDNA was captured in these RNA Pol II antibody coated wells compared to the corresponding wells coated with anti mouse IgG antibody. Again, this is a prove that the described single-tube ChIP can be used to enrich protein bound nucleic acids and that this bound nucleic acids can be detected and quantified in the same tube without prior purification of the nucleic acid.

A combination of a low salt buffer and a TE buffer (comprising Tris and EDTA) is particularly useful in conjunction with the present invention. This was surprising, as they are no typical washing buffers.

The invention claimed is:

1. A method for analyzing interactions of a nucleic acid with at least one polypeptide, comprising
    (a) providing a reaction vessel with a composition comprising cross-linked complexes comprising at least one nucleic acid and at least one polypeptide;
    (b) immobilizing at least part of the cross-linked complexes to the reaction vessel;
    (c) at least partially reversing said cross-links in said immobilized complexes by performing a heat incubation step thereby at least partially releasing the nucleic acids from the complexes; and
    (d) performing an amplification reaction to identify the released nucleic acid;
    wherein steps (a) to (d) are performed in the same reaction vessel.

2. The method according to claim 1, wherein the nucleic acid released in the cross-link reversing step (c) is not isolated and/or purified prior to step (d).

3. The method according to claim 1, wherein steps (c) and d) are performed as elements of a HotStart polymerase chain reaction protocol.

4. The method according to claim 1, wherein said reaction vessel carries at least one immobilized capture agent specific for a component of said complexes comprising at least one nucleic acid and at least one polypeptide.

5. The method according to claim 1, wherein said cross-linked complexes are contacted with a capture agent specific for a component of said complexes comprising at least one nucleic acid and at least one polypeptide and wherein a reaction vessel is used which carries at least one linking agent specific for the capture agent.

6. The method according to claim 1, wherein the reaction vessel carries at least two different capture and/or linking agents.

7. The method according to claim 1, wherein the method is performed in a multiplex format, wherein several reaction vessels are used which carry different capture agents and/or linking agents.

8. The method according to claim 4, wherein the reaction vessel(s) is/are provided with the capture agents and/or the linking agents by coating the reaction vessel(s) with the capture agents and/or the linking agents.

9. The method according to claim 1, wherein in step (c) the heat incubation step is performed for at least 5 min, and the temperature used in the heat incubation step is $\geq 80°$ C.

10. The method according to claim 1, wherein the composition comprising cross-linked complexes comprising at least one nucleic acid and at least one polypeptide is obtained by
    (a) incubating cells containing at least one complex comprising a nucleic acid and at least one polypeptide with a reversible cross-linking agent;
    (b) optionally stopping the cross-linking reaction; and
    (c) lysing said cells and shearing said nucleic acid.

11. A method of identifying interactions of a nucleic acid with at least one polypeptide comprising:
    (a) providing a reaction vessel comprising at least one capture agent specific for a polypeptide of interest wherein said capture agent is immobilized to the reaction vessel, wherein at least some of the specific binding regions of the capture agent are orientated towards the opening of the reaction vessel, with a composition comprising cross-linked complexes comprising at least one nucleic acid and at least one polypeptide of interest;
    (b) immobilizing at least part of the cross-linked complexes to the reaction vessel;
    (c) at least partially reversing said cross-links in said immobilized complexes by performing a heat incubation step thereby at least partially releasing the nucleic acids from the complexes; and
    (d) performing an amplification reaction to identify the released nucleic acid,
    wherein steps (a) to (d) are performed in the same reaction vessel.

12. The method according to claim 1, wherein in step (c) the heat incubation step is performed for at least 10 min, and the temperature used in the heat incubation step is $\geq 90°$ C.

13. The method according to claim 1, wherein in step (c) the heat incubation step is performed for at least 15 min, and the temperature used in the heat incubation step is $\geq 94°$ C.

14. The method according to claim 1, wherein in step (c) the heat incubation step is performed for at least 20 min, and the temperature used in the heat incubation step is $\geq 94°$ C.

* * * * *

UNITED STATES PATENT AND TRADEMARK OFFICE
CERTIFICATE OF CORRECTION

PATENT NO. : 8,536,100 B2  Page 1 of 1
APPLICATION NO. : 12/922366
DATED : September 17, 2013
INVENTOR(S) : Frank Narz It is certified that error appears in the above-identified patent and that said Letters Patent is hereby corrected as shown below:

In title page, item (75) Inventor:, delete "Franz Narz" and insert --Frank Narz-- therefor.

Signed and Sealed this
Twenty-ninth Day of October, 2013

Teresa Stanek Rea
*Deputy Director of the United States Patent and Trademark Office*